United States Patent [19]

Jaeb et al.

[11] Patent Number: 5,094,239
[45] Date of Patent: Mar. 10, 1992

[54] COMPOSITE SIGNAL IMPLEMENTATION FOR ACQUIRING OXIMETRY SIGNALS

[75] Inventors: Jonathan P. Jaeb; Ronald L. Branstetter, both of San Antonio, Tex.

[73] Assignee: Colin Electronics Co., Ltd., Japan

[21] Appl. No.: 417,320

[22] Filed: Oct. 5, 1989

[51] Int. Cl.⁵ .............................................. A61B 5/00
[52] U.S. Cl. ....................................... 128/633; 356/41
[58] Field of Search .................... 128/633, 664; 356/41

[56] References Cited

U.S. PATENT DOCUMENTS

| | | | |
|---|---|---|---|
| 4,573,778 | 3/1986 | Shapiro et al. | 351/219 |
| 4,773,422 | 9/1988 | Isaacson et al. | 128/633 |
| 4,869,254 | 9/1989 | Stone et al. | 128/633 |
| 4,877,084 | 10/1989 | Atkins et al. | 128/664 |
| 4,934,372 | 6/1990 | Corenman et al. | 128/633 |

Primary Examiner—William E. Kamm
Assistant Examiner—Kevin Pontius
Attorney, Agent, or Firm—Oliff & Berridge

[57] ABSTRACT

An oximeter system for measuring blood oxygen saturation using a noninvasive optical technique is disclosed. A patient's arterial blood is illuminated with light at two different wavelengths and the intensity of the light which is transmitted through or reflected by said arterial blood is correlated with the blood oxygen saturation of the tissue. The system provides a manner in which filtering artifacts are avoided in the oximeter signal using a high resolution analog-to-digital converter of 14 bits or more, such that, it is unnecessary to separate the DC and pulsatile components of the oximeter signal prior to processing within the microprocessor.

4 Claims, 3 Drawing Sheets

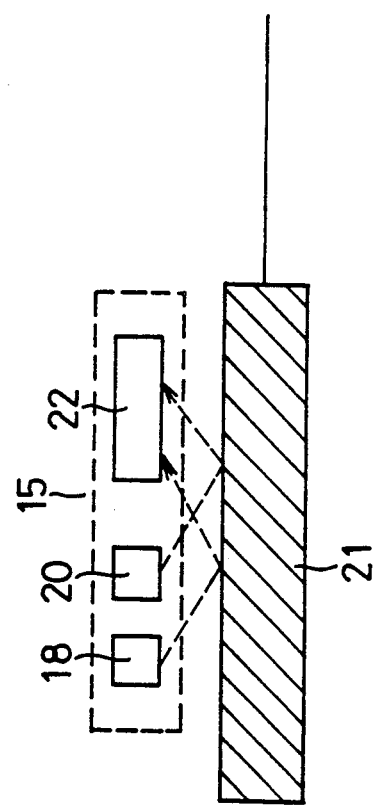

COMPOSITE SIGNAL IMPLEMENTATION FOR ACQUIRING OXIMETRY SIGNALS

BACKGROUND OF THE INVENTION

A pulse oximeter estimates the degree of oxygen saturation of the hemoglobin in the arterial blood ($SaO_2$). Modern instruments use optical techniques in conjunction with a noninvasive sensor to achieve the estimate. The sensor of the oximeter radiates a section of well perfused tissue with at least two wavelengths of light. The light contacts hemoglobin contained in red blood cells. A certain amount of light is absorbed by the hemoglobin. The amount of light absorbed depends on the wavelength of light and whether the hemoglobin is oxygenated. By knowing the wavelength of light being used and the relative amount of light being absorbed, it is possible to estimate $SaO_2$. The amount of light being absorbed is typically determined in pulse oximeters by comparing the amount of return light detected at systole and at diastole. The difference between these two readings is determined for each wavelength. This difference is assumed to be the light absorbed by the hemoglobin in the oxygenated blood.

In previous systems, taking these light measurements involves using a photodetector which is sensitive to both wavelengths of incident light, to provide an electrical signal. This signal is then filtered to remove the non-changing or DC components. The remaining pulsatile component is then amplified, filtered to remove noise, and typically converted to digital format for processing. The difference between the light measurements is generally computed in software, although it would be possible to use peak detectors and difference circuits to perform the calculation in analog.

Available commercial pulse oximeters place the sensor's light source on the opposite side of an appendage from the detector. In this manner, all light received by the detector has been transmitted through the appendage. There are several disadvantages to placing an oximetry sensor on an appendage. For example, if the patient goes into shock, the extremities are the first to lose blood flow. If blood flow is lost, the oximeter cannot estimate $SaO_2$.

Recently, a pulse oximeter sensor as shown in FIG. 3 has been developed that uses reflected rather than transmitted light to estimate $SaO_2$. The sensor 15 for this device has light sources 18 and 20 of different wavelengths positioned on the same side of the tissue 21 as the detector 22. With this arrangement, the detector receives only that light that is scattered back (reflected) to the detector 22. The advantage of the reflectance oximeter is that it is not limited to being located on appendages.

A major problem encountered in the implementation of a reflectance oximeter is obtaining accurate readings of the signals returned from the tissue. The difficulty lies in detecting and accurately measuring the extremely low amplitude pulsatile signals which are riding on top of very large levels of non-pulsatile or DC signals. For reflectance measurements, the ratio of pulsatile to DC components of the return signals can be anywhere from 5% to less than 1%.

The algorithms used to determine the oxygen saturation from reflectance signals require as inputs accurate measurements of not only the pulsatile components, but also the DC components. Each of these signals are generally required to be measured within an accuracy of at least 1%. In addition, the exact relationship of the pulsatile to DC signals in terms of gain, time, and frequency response must be controlled and known. Furthermore, the low ratio of pulsatile to DC components in the reflectance signal makes the system much more sensitive to errors introduced to the signal by the signal conditioning and conversion.

Thus, there remains a strong need in the art for an improved oximeter system which avoids erroneous blood oxygen saturation measurements as a result of errors introduced when separating the DC and pulsatile components of the oximeter sensor signal prior to microprocessor analysis.

SUMMARY OF THE INVENTION

Accordingly, the present invention has been developed to overcome the foregoing shortcomings of existing oximeters.

It is therefore an object of the present invention to provide an oximeter which removes filtering artifacts from an oximetry signal.

It is yet another object of the present invention to provide an oximeter which does not require separating the composite electrical signal from the oximeter sensor into its DC and pulsatile components.

Thus, in accordance with the present invention an oximeter is provided having means for illuminating the patient's arterial blood with two different wavelengths, means for measuring the intensity of the light after contact with the blood, and data processing means for correlating the intensity of the measured light with the blood oxygen saturation of the patient, wherein the data processing means includes an analog-to-digital converter having a resolution of 14 bits or more for converting an electrical output signal, indicative of the intensity of the measured light, into digital form prior to any separation of said electrical output into its DC and pulsatile components.

BRIEF DESCRIPTION OF THE DRAWINGS

The preferred embodiments are described with reference to the drawings in which:

FIG. 3 is a block diagram of a reflectance oximeter sensor in accordance with the present invention.

DETAILED DESCRIPTION OF THE PREFERRED EMBODIMENT

The traditional approach to acquiring oximetry signals has been to split the composite electrical signal into separate components, DC and pulsatile. Each component is then filtered and amplified to allow it to be accurately converted by an Analog-to-Digital Converter (ADC). The pulsatile and DC components of a given signal are sampled as quickly as possible to minimize any time differences, and the frequency responses of the filters are controlled as precisely as practicable.

Figure 1:
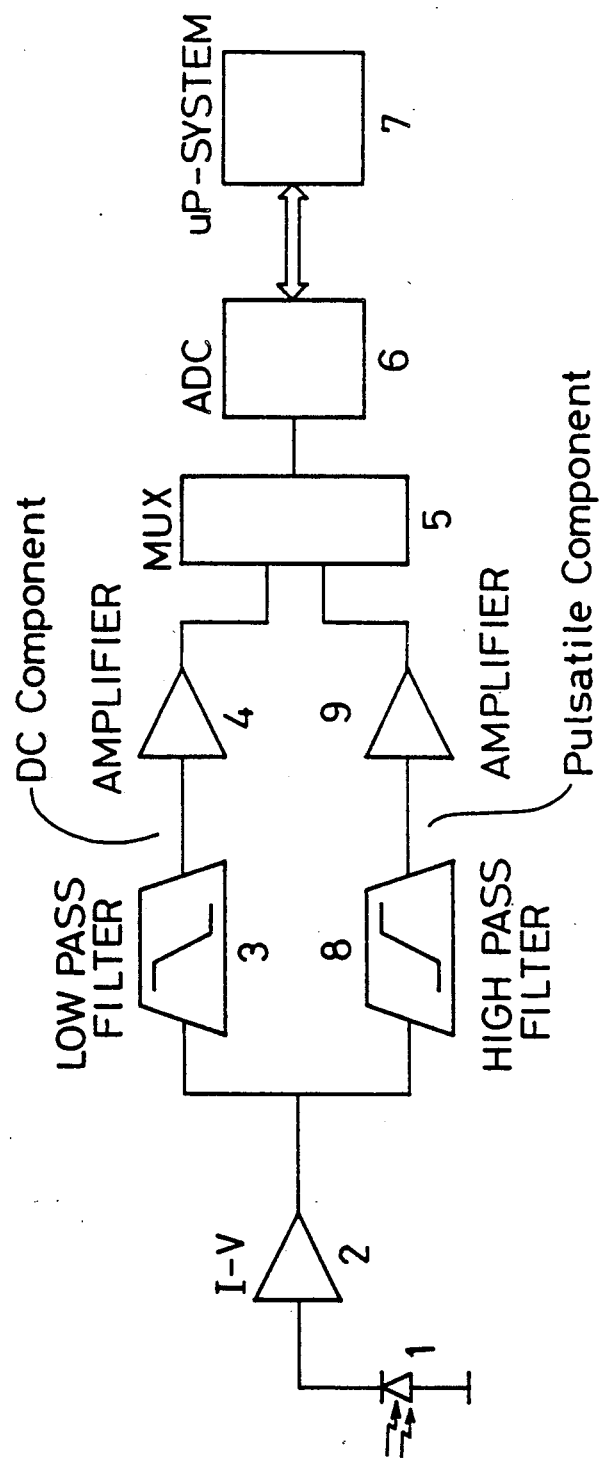
FIG. 1 is a schematic block diagram of one channel of a traditional oximeter system.

Referring to FIG. 1, the traditional approach utilizes a photodetector 1 to detect the light. The current output of this device is converted to a voltage using an op-amp in a current-to-voltage (I-V) configuration 2. The output is then fed into two separate filter channels. The first is a low-pass filter 3 which is set to pass only (ideally) the DC component of the signal. This DC signal is then amplified 4 and passed through a multiplexer 5 to the ADC 6. The digital data is then fed to the microprocessor system 7, for oxygen saturation calculation using methods known to one of ordinary skill in the art. The output of the I-V configuration 2 is also fed into a high pass filter 8 to remove the DC component, leaving only the pulsatile component. This signal is also amplified 9 and fed through the multiplexer 5 to the ADC 6. To realize a complete oximeter it will be known to one of ordinary skill in the art that two channels of the above described electronics are required, one for each wavelength.

There is a practical limit to the accuracy of the traditional approach due to the fact that errors are introduced to the signals by the filters 3 and 8 used to separate the DC and pulsatile components. Since the two signal components go through different amplifiers and filters, there are slight differences in the gains and transfer functions of the filters. Additionally, there are small changes in the above parameters due to component value drift with time. Finally, filtering the DC from the pulsatile component requires the use of a very low frequency, high pass filter 8, with an inherently long response time. This response time slows the instrument's recovery from transient signals such as those produced from motion artifacts.

The present invention overcomes these shortcomings by not splitting the composite electrical signal into its separate components. Instead, the present invention converts the entire composite signals to digital form using an ADC with a resolution of 14 bits or more (i.e., at least 14 bits). This approach requires amplifying and filtering the composite signal using commercially available analog electronics that are low noise and have high dynamic overhead so as to preserve the quality of the small pulsatile component while amplifying it to reasonable levels. Since the pulsatile signal must be acquired to within 1% accuracy, and since it can be as small as 1% of the overall composite signal, the ADC and associated electronics must provide a resolution of 1:10,000 or more.

Figure 2:
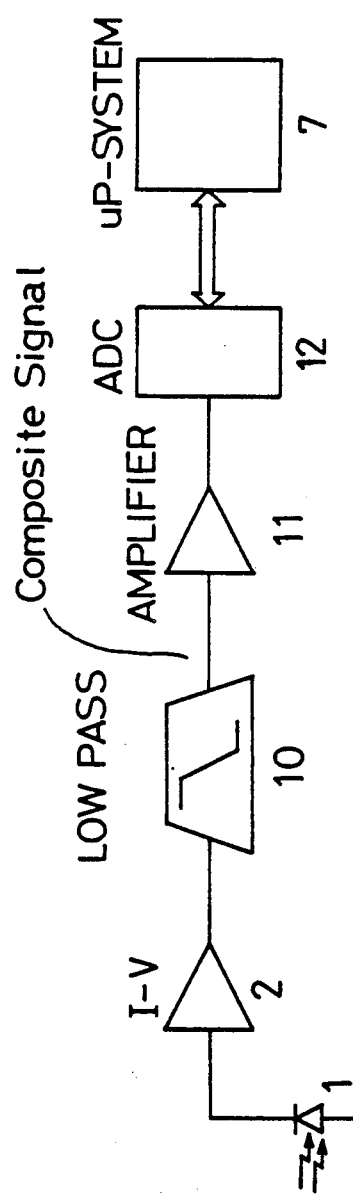
FIG. 2 is a schematic block diagram of one channel of an oximeter system in accordance with the present invention.

Referring to FIG. 2, the preferred embodiment of the present invention includes a photodetector 1 connected to the I-V 2 as before, which feeds directly into a low pass filter 10 to remove high frequency noise. The output of the filter 10 is further amplified 11 and input to the high resolution ADC 12. The data now in digital format is then transferred to the microprocessor system 7 for oxygen saturation calculation. As in the traditional approach, two channels, one for each wavelength, would be required to implement a complete oximeter.

The advantages of the present invention stem primarily from the fact that the exact same filters and amplifiers operate on both DC and pulsatile components of the composite signal. By definition, both components will have the same applied gain. The filter response is no longer critical since it operates on both components and the recovery time from motion artifacts can be greatly improved since a low frequency, high pass filter is not required. Since a single sample acquires both components, there can be no time-skew related errors. Once the composite signal has been converted, the data is processed in the software where the components can be separated, filtered and ratioed in order to determine blood oxygen saturation using precisely defined and completely controlled functions.

Modifications and variations to the invention will be apparent to those skilled in the art from the foregoing disclosure and teachings. It is therefore to be understood that, within the scope of the appended claims, the invention may be practiced otherwise than as specifically described. Thus, while only certain preferred embodiments of the invention have been specifically described herein, it will be apparent that numerous modifications may be made thereto without departing from the spirit and scope of the invention as defined in the appended claims.

What is claimed is:

1. A blood oxygen saturation monitoring system for non-invasive measurement of oxygen saturation in the blood of a subject comprising:

a first source of electromagnetic radiation at a first wavelength;

a second source of electromagnetic radiation at a second wavelength;

means for positioning said first and second sources of electromagnetic radiation to illuminate a sample of blood in tissue;

detecting means for receiving electromagnetic radiation transmitted through or reflected from said sample of blood, and for providing an electrical output signal indicative of the intensity of said detected electromagnetic radiation for each of said wavelengths; and data processing means for correlating said detected electromagnetic radiation with the blood oxygen saturation of said tissue, said data processing means comprising:

low pass filter means for removing high frequency noise from the electrical output signal of said detecting means;

amplifier means for amplifying said electrical output signal;

analog-to-digital converter means having a resolution of at least 14 bits, for converting said electrical output signal into digital data prior to any separation of said electrical output signal into a DC component and a pulsatile component; and processing means for processing said digital data by separating said digital data into said DC component and said pulsatile component for each of said wavelengths and for producing a ratio of said pulsatile component to said DC component for each of said wavelengths and for determining said blood oxygen saturation based on said ratios.

2. A blood oxygen saturation monitoring system having a plurality of electromagnetic sources for illuminating a sample of blood in tissue, each of said sources operating at a different wavelength, having a means for attaching said electromagnetic sources proximate to said tissue and having processing circuitry, said processing circuitry comprising:

a photodetector receiving composite signals each having a DC and a pulsatile component from said electromagnetic sources reflected from or transmitted through said tissue and generating a plurality of composite current signals, each having a DC and pulsatile component, in response to detection of said composite signals;

a first converter means coupled to said photodetector for converting said composite current signals to a plurality of composite voltage signals, each of said composite voltage signals having a DC component and a pulsatile component;

a low pass filter coupled to said first converter means removing high frequency noise components from said composite voltage signals;

an amplifier coupled to said low pass filter having a gain wherein said DC component and said pulsatile component contained within said composite voltage signals are amplified by exactly said gain;

second converter means coupled to said amplifier for converting said composite voltage signals to digital data having both DC component and pulsatile component information prior to any separation of the DC and pulsatile components of said composite voltage signals; and processing means coupled to said second converter means for processing said digital data and for determining said blood oxygen saturation based on the ratios of said DC and pulsatile components.

3. The blood oxygen saturation monitoring system of claim 2, wherein said second converter means comprises an analog-to-digital converter having at least 14 bits of resolution.

4. The blood oxygen saturation monitoring system of claim 2, wherein said low pass filter and said amplifier are low noise analog circuits.

* * * * *